United States Patent
Sugimoto et al.

(10) Patent No.: US 8,993,584 B2
(45) Date of Patent: Mar. 31, 2015

(54) CONTROL AGENT FOR SOFT ROT AND CONTROL METHOD FOR THE SAME

(75) Inventors: Koji Sugimoto, Kusatsu (JP); Hiroyuki Hayashi, Kusatsu (JP)

(73) Assignee: Ishihara Sangyo Kaisha, Ltd., Osaka-shi (JP)

( * ) Notice: Subject to any disclaimer, the term of this patent is extended or adjusted under 35 U.S.C. 154(b) by 0 days.

(21) Appl. No.: 13/810,536

(22) PCT Filed: Jul. 21, 2011

(86) PCT No.: PCT/JP2011/004124
§ 371 (c)(1),
(2), (4) Date: Jan. 16, 2013

(87) PCT Pub. No.: WO2012/011287
PCT Pub. Date: Jan. 26, 2012

(65) Prior Publication Data
US 2013/0123287 A1    May 16, 2013

(30) Foreign Application Priority Data

Jul. 23, 2010  (JP) ................. 2010-166427
Nov. 18, 2010  (JP) ................. 2010-257612

(51) Int. Cl.
| | |
|---|---|
| *A01N 43/54* | (2006.01) |
| *A01N 43/50* | (2006.01) |
| *A01N 43/56* | (2006.01) |
| *A01N 41/06* | (2006.01) |
| *A01N 37/34* | (2006.01) |
| *A01N 37/50* | (2006.01) |
| *A01N 37/32* | (2006.01) |
| *A01N 43/36* | (2006.01) |
| *A01N 43/40* | (2006.01) |
| *A01N 43/653* | (2006.01) |
| *A01N 47/34* | (2006.01) |
| *A01N 47/38* | (2006.01) |
| *A01N 47/44* | (2006.01) |
| *A01N 53/00* | (2006.01) |
| *A01N 43/38* | (2006.01) |

(52) U.S. Cl.
CPC ............... *A01N 43/54* (2013.01); *A01N 37/32* (2013.01); *A01N 37/34* (2013.01); *A01N 37/50* (2013.01); *A01N 41/06* (2013.01); *A01N 43/36* (2013.01); *A01N 43/40* (2013.01); *A01N 43/50* (2013.01); *A01N 43/56* (2013.01); *A01N 43/653* (2013.01); *A01N 47/34* (2013.01); *A01N 47/38* (2013.01); *A01N 47/44* (2013.01); *A01N 53/00* (2013.01); *A01N 43/38* (2013.01)
USPC ........... 514/269; 514/398; 514/383; 514/399; 544/319; 548/526; 548/513; 548/330

(58) Field of Classification Search
USPC .......... 514/269, 383, 421, 396; 548/263, 336, 548/513; 544/319
See application file for complete search history.

(56) References Cited

U.S. PATENT DOCUMENTS

| | | |
|---|---|---|
| 3,965,109 A | 6/1976 | Tomlin et al. |
| 2002/0013350 A1* | 1/2002 | Nishiguchi et al. ........... 514/354 |
| 2009/0143452 A1 | 6/2009 | Bruns et al. |

FOREIGN PATENT DOCUMENTS

| | | |
|---|---|---|
| CN | 101175615 A | 5/2008 |
| DE | 1203533 B | 10/1965 |
| EP | 0976326 A1 | 2/2000 |
| EP | 1943901 A2 | 7/2008 |
| EP | 2143709 A1 | 1/2010 |
| EP | 2154124 A1 | 2/2010 |
| JP | 53-35127 | 9/1978 |
| WO | WO-2007/104677 A1 | 9/2007 |
| WO | WO-2010/146791 A2 | 12/2010 |

OTHER PUBLICATIONS

Snijder et al European Journal of Plant Pathology 108: 565-571, 2002.*
Czajkowski et al (2011) Control of blackleg and tuber soft rot of potato caused by *Pectobacterium* and *Dickeya* species.*
Database WPI Week 197743 Thomson Scientific, London, GB; AN 1977-76380Y, XP002665924,-& JP 50 123827A (Hatano S), Sep. 29, 1975 (1 page).
Database WPI Week 201021 Thomson Scientific, London, GB; AN 2010-C52871 XP002665925, -& CN 101 653 132A (Dongguan Reid Feng Biology Sci & Technol) Feb. 35, 2010 (2 pages).
Database CA [Online], Parashar R. D. et al, "Efficacy of Klorocin and other chemicals in controlling soft rot of Potato in field and storage," XP002665926, retrieved from STN Database accession No. 112:134380 abstract Indian Journal of Mycology and Plant Pathology, 1988, 18(1), 39-42 ISSN: 0303-4097 (2 pages).
Database CA [Online] Rathaiah, Y., "Control of soft rot of ginger with Ridomil," XP002665927, retrieved from STN Database accession No. 108:89380 abstract,Pesticides, 1987, 21(12), 29-30 ISSN: 0031-6148 (2 pages).
Database CA [Online] Bhagwat, V.Y., "Control of soft rot of ginger," XP002665928, retrieved from STN Database accession No. 55:127021, abstract, Poona Agricultural College Magazine, 1960, 51, 47-9 CODEN: PACMA9; ISSN: 0032-4299 (2 pages).

(Continued)

*Primary Examiner* — Shirley V Gembeh
(74) *Attorney, Agent, or Firm* — Locke Lord LLP

(57) ABSTRACT

Providing a novel control agent for soft rot and a novel control method for the same.
A compound having no antibacterial activity against *Erwinia carotovora* but having a control activity against fungi on soil surface, specifically containing, as the active ingredient, a fungicide comprising any of a strobilurin compound such as azoxystrobin and kresoxim-methyl, an azole compound such as triflumizol, cyazofamid, amisulbrom, and thiophanate-methyl, a carboxamide compound such as penthiopyrad and boscalid, a sulfonamide compound such as flusulfamide, an organic chlorine compound such as chlorothalonil, a dicarboximide compound such as procymidone and iprodione, a phenylpyrrole compound such as fludioxonil, an anilinopyrimidine compound such as mepanipyrim, and a guanidine compound such as iminoctadine is the control agent for plant soft rot, which is applied to plant cultivation soil.

11 Claims, No Drawings

(56) References Cited

OTHER PUBLICATIONS

International Search Report dated Feb. 14, 2012, issued for PCT/JP2011/004124.

L-H. Cheah et al., "Soil-Incorporation of Fungicides for Control of Clubroot of Vegetable *Brassicas*," New Zealand Plant Protection Society (Inc.), Proc. 51st N.Z. Plant Protection Conf.,199, pp. 130-133.

Office Action dated Jan. 28, 2014, issued for the Chinese patent application No. 201180045884.7 and Japanese translation thereof.

"Changes in aromatic amide germicides—from carboxin, mepronil, flutolanil, to penthiopyrad and boscalid", World Pesticides, vol. 29, 1, pp. 1-7, Feb. 2007.

Chen et al, "Incidence and Control of Soft Rot of Chinese cabbage", China Academic Journal Electronic Publishing House, No. 1, Jan. 10, 2009, p. 143 and p. 145.

Chi Hui-wei et al, "Synthesis and Bioactivity of Fungicide Boscalid", Fine Chemical Intermediates, No. 37 No. 4, Aug. 15, 2007, pp. 14-16.

Office Action dated Aug. 21, 2014, issued for the corresponding Chinese patent application No. 201180045884.7, Japanese translation thereof and partial English translation thereof.

\* cited by examiner

CONTROL AGENT FOR SOFT ROT AND CONTROL METHOD FOR THE SAME

TECHNICAL FIELD

The present invention relates to a control agent for soft rot of a plant such as a vegetable, and a control method for soft rot using the control agent.

BACKGROUND OF THE INVENTION

Soft rot is a plant disease which is caused by *Erwinia carotovora* and causes plant tissues to become soft and rotten. Examples of a plant to be a target for controlling soft rot include vegetables such as cabbage, celery, Japanese radish, tobacco, onion, tomato, carrot, Chinese cabbage, potato, lettuce, wasabi, and the like. Since a pesticide is rarely effective in a bacterial disease, an antibiotic such as streptomycin or a copper-based bactericide as described in Patent reference 1 is conventionally applied to a target plant to effect disease control. However, an antibiotic which has been used for controlling a bacterial disease such as soft rot is expensive and also has a problem that resistant bacteria appear. Further, in the case of using a copper-based bactericide, there are problems that (1) when the air temperature is high, phytotoxicity occurs; (2) a disease control effect is not obtained unless a large amount of the bactericide is used, and it raises a concern that metal contamination occurs; and the like. Therefore, the development of a disease control method which solves the problems of the antibiotic and the copper-based pesticide has been demanded.

CITATION LIST

Patent Literature

[Patent Literature 1] PTL 1:JP-B-53-35127

SUMMARY OF THE INVENTION

Control agents having been used conventionally against soft rot have some practical problems such as high cost, the occurrence of phytotoxicity, or insufficient control effects on plant diseases and damages depending on the applied condition. The problems to be solved in accordance with the invention are to provide a control agent for soft rot and a control method for soft rot, which can solve the problems described above.

Problems that the Invention is to Solve

So as to solve the problems, the inventors made intensive studies, and as a result, they unexpectedly found that a compound having no antibacterial activity against *Erwinia carotovora* but having a control activity against fungi on soil surface showed no bactericidal effect when directly applied to *Erwinia carotovora* but exerted a control effect against soft rot when applied to soil for plant cultivation, the compound specifically including at least one fungicide selected from the group consisting of strobilurin compounds such as methyl=(E)-2-{2-[6-(2-cyanophenoxy)pyrimidin-4-yloxy]phenyl}-3-methoxyacrylate (the common name: azoxystrobin; the compound is hereinbelow expressed under the common name) and methyl=(E)-methoxyimino[2-(o-tolyloxymethyl)phenyl]acetate (common name: kresoxim-methyl; the compound is expressed hereinbelow under the common name), azole compounds such as (E)-4-chloro-alpha,alpha,alpha-trifluoro-N-[1-imidazol-1-yl-2-propoxyethylidene]-o-toluidine (common name: triflumizole; the compound is hereinbelow expressed under the common name), 4-chloro-2-cyano-N,N-dimethyl-5-p-tolylimidazole-1-sulfoneamide (common name: cyazofamid; the compound is expressed hereinbelow under the common name), 3-[(3-bromo-6-fluoro-2-methyl-1H-indol-1-yl)sulfonyl]-N,N-dimethyl-1H-1,2,4-triazole-1-sulfoneamide (common name: amisulbrom; the compound is hereinbelow expressed under the common name), dimethyl=4,4'-(o-phenylene)bis(3-thioallophanate) (common name: thiophanate-methyl; the compound is expressed hereinbelow under the common name), carboxamide compounds such as (RS)—N-[2-(1,3-dimethylbutyl)-3-thienyl]-1-methyl-3-(trifluoromethyl)-1H-pyrazole-4-carboxamide (common name: penthiopyrad; the compound is expressed hereinbelow under the common name), and 2-chloro-N-(4'-chlorobiphenyl-2-yl)nicotinamide (common name: boscalid; the compound is expressed hereinbelow under the common name), sulfonamide compounds such as 2',4-dichloro-alpha,alpha,alpha-trifluoro-4'-nitro-m-toluenesulfone anilide (common name: flusulfamide; the compound is expressed hereinbelow under the common name), organic chlorine compounds such as 2,4,5,6-tetrachloro-1,3-benzene dicarbonitrile (common name: chlorothalonil; the compound is hereinbelow expressed under the common name), dicarboximide compounds such as N-(3,5-dichlorophenyl)-1,2-dimethylcyclopropane-1,2-dicarboximide (common name: procymidone; the compound is hereinbelow expressed under the common name) and 3-(3,5-dichlorophenyl)-N-isopropyl-2,4-dioxoimidazolizine-1-carboxamide (common name: iprodione; the compound is expressed hereinbelow under the common name), phenylpyrrole compounds such as 4-(2,2-difluoro-1,3-benzodioxol-4-yl)pyrrole-3-carbonitrile (common name: fludioxonil; the compound is expressed hereinbelow under the common name), anilinopyrimidine compounds such as N-(4-methyl-6-prop-1-ynylpyrimidin-2-yl)aniline (common name: mepanipyrim; the compound is expressed hereinbelow under the common name), and guanidine compounds such as 1,1'-iminodi(octamethylene)diguanidinium=tris(alkylbenzenesulfonate)(common name: iminoctadine albesilate salt; the compound is expressed hereinbelow under the common name).

The control agent for plant soft rot in accordance with the invention is made on the basis of the finding described above. The invention relates to a control agent for plant soft rot, containing as the active ingredient a compound with no antibacterial activity against *Erwinia carotovora* but with a control activity against fungi on soil surface (sometimes referred to as "the active ingredient of the invention" hereinbelow), specifically including at least one fungicide selected from the group consisting of strobilurin compounds, azole compounds, carboxamide compounds, sulfonamide compounds, organic chlorine compounds, dicarboximide compounds, phenylpyrrole compounds, anilinopyrimidine compounds, and guanidine compounds. The control agent includes the control agent for plant soft rot as described above, which is a control agent to be applied to soil for plant cultivation.

The invention also relates to a control method for plant soft rot, comprising applying an active dose of the active ingredient of the invention to soil for plant cultivation. The method includes a control method for plant soft rot comprising applying an effective amount of the active ingredient of the invention to soil for plant cultivation and subsequently sowing plant seeds or permanently planting plant seedlings, and a control method for plant soft rot, comprising applying an effective amount of the active ingredient of the invention to the surface of cultivation soil, without mixing in cultivation soil. Furthermore, the control method for plant soft rot includes the control method for plant soft rot as described above, where the dose of the active ingredient of the invention to be applied to cultivation soil is 0.025 to 2.5 g/m².

Further, the invention includes control agents for soft rot of a plant and control methods for the same, wherein, in the above-mentioned control agent for soft rot of a plant and control method for the same, the plant is a vegetable, and the vegetable is at least one kind selected from the group consisting of asparagus, endive, calla, cauliflower, cabbage, amorphophallus konjac, *Brassica campestris*, celery, Japanese radish, tobacco, onion, qing-geng-cai, tomato, eggplant, carrot, green onion, Chinese cabbage, *Brassica oleracea*×*Brassica campestris*, parsley, potato, broccoli, rakkyo, lettuce, wasabi, and oil-seed rape.

Furthermore, the invention encompasses the control agent for soft rot or the control method for soft rot, where the strobilurin compound is azoxystrobin or kresoxim-methyl; the azole compound is triflumizole, cyazofamid, amisulbrom or thiophanate-methyl; the carboxamide compound is penthiopyrad or boscalid; the sulfonamide compound is flusulfamide; the organic chlorine compound is chlorothalonil; the dicarboximide compound is procymidone, or iprodione; the phenylpyrrole compound is fludioxonil; the anilinopyrimidine compound is mepanipyrim; and the guanidine compound is iminoctadine albesilate salt.

Advantages of the Invention

In accordance with the invention, a control effect against soft rot at the same level or at a higher level than the levels exerted by conventional methods can be obtained, using a compound with no antibacterial activity against *Erwinia carotovora* but with a control activity against fungi on soil surface, the compound specifically including at least one fungicide selected from the group consisting of strobilurin compounds, azole compounds, carboxamide compounds, sulfonamide compounds, organic chlorine compounds, dicarboximide compounds, phenylpyrrole compounds, anilinopyrimidine compounds, and guanidine compounds as a control agent for soft rot to be applied to cultivation soil of plants. By applying the compound to the surface of cultivation soil without mixing in cultivation soil, the concentration of the compound on the surface of the cultivation soil is kept high to more efficiently exert the control effect against soft rot. According to conventional control methods for soft rot, further, dusting powders for stems and leaves are generally sprayed about three times. In accordance with the invention, in contrast, the treatment is done only once, which saves laborious works.

MODE FOR CARRYING OUT THE INVENTION

In the control agent for soft rot and the control method for soft rot in accordance with the invention, a compound with no antibacterial activity against *Erwinia carotovora* but with a control activity against fungi on soil surface is used as the active ingredient.

The phrase "with no antibacterial activity against *Erwinia carotovora*" means no inhibition of the growth of *Erwinia carotovora*, more specifically meaning that the control agent at 1000 ppm never inhibits the growth of *Erwinia carotovora*. An inhibition test of the growth of *Erwinia carotovora* may be done according to known methods. For example, the inhibition test is satisfactorily done by the method described in the present description.

The phrase "with a control activity against fungi on soil surface" means that the control agent has a control activity against fungi existing on soil surface (for example, fungi causing plant diseases and damages). Specific examples of the active ingredient of the invention include at least one fungicide selected from the group consisting of strobilurin compounds, azole compounds, carboxamide compounds, sulfonamide compounds, organic chlorine compounds, dicarboximide compounds, phenylpyrrole compounds, anilinopyrimidine compounds, and guanidine compounds.

The compound as the active ingredient of the fungicide (under the common name; some compounds under application are also included: or under the test code according to the Japan Plant Protection Association) is now exemplified below.

The strobilurin compounds include for example azoxystrobin, kresoxim-methyl, metominostrobin, trifloxystrobin, picoxystrobin, oryzastrobin, dimoxystrobin, pyraclostrobin, fluoxastrobin, and enestroburin. Among them, azoxystrobin and kresoxim-methyl are preferable.

The azole compounds include for example triadimefon, bitertanol, triflumizole, etaconazole, propiconazole, penconazole, flusilazole, myclobutanil, cyproconazole, tebuconazole, hexaconazole, furconazole-cis, prochloraz, metconazole, epoxiconazole, tetraconazole, oxpoconazole fumarate, sipconazole, prothioconazole, triadimenol, flutriafol, difenoconazole, fluquinconazole, fenbuconazole, bromuconazole, diniconazole, tricyclazole, probenazole, simeconazole, pefurazoate, ipconazole, imibenconazole, benomyl, thiophanate-methyl, carbendazim, thiabendazole, fuberiazole, cyazofamid, imazalil, and amisulbrom (amibromdole as the other name). Among them, triflumizole, cyazofamid, amisulbrom and thiophanate-methyl are preferable.

The carboxamide compounds include for example carboxin, oxycarboxin, thifluzamide, penthiopyrad, boscalid, bixafen, fluopyram, isotianil, mixtures of 3-(difluoromethyl)-1-methyl-N-[(1RS, 4SR, 9RS)-1,2,3,4-tetrahydro-9-isopropyl-1,4-methanonaphthalen-5-yl]pyrazole-4-carboxa mide and 3-(difluoromethyl)-1-methyl-N-[(1RS, 4SR, 9SR)-1,2,3, 4-tetrahydro-9-isopropyl-1,4-methanonaphthalen-5-yl]pyrazole-4-carboxa mide (isopyrazam), dimethomorph, flumorph, and S-2200. Among them, penthiopyrad and boscalid are preferable.

The sulfonamide compounds include for example flusulfamide.

The organic chlorine compounds include for example fthalide, chlorothalonil, and quintozene. Among them, chlorothalonil is preferable.

The dicarboximide compounds include for example procymidone, iprodione and yinclozolin. Among them, procymidone and iprodione are preferable.

The phenylpyrrole compounds include for example fludioxonil, and fenpiclonil.

Among them, fludioxonil is preferable.

The anilinopyrimidine compounds include for example mepanipyrim, pyrimethanil, cyprodinil, and ferimzone. Among them, mepanipyrim is preferable.

The guanidine compounds include for example iminoctadine, dodine, iminoctadine albesilate salt, and iminoctadine acetate salt. Among them, iminoctadine albesilate salt is preferable.

As the active ingredient of the invention, one type or two or more types of the active ingredient are appropriately selected and used.

The control agent for soft rot in accordance with the invention may be prepared as various formulations such as emulsifiable concentrate, dust formulation, wettable powder, liquid formulation, granule, and suspension-concentrate by blending various types of auxiliary agents with the active ingredient of the invention according to general formulation methods of agrichemicals. In that case, the active ingredient of the invention and the above-mentioned auxiliary agents may be mixed all together and formulated into a preparation, or they may be separately formulated into different preparations and the resulting preparations may be mixed with each other. Examples of the auxiliary agents as used herein include a carrier, an emulsifying agent, a suspending agent, a thickening agent, a stabilizing agent, a dispersing agent, a spreading agent, a wetting agent, a penetrating agent, an antifreezing agent, an antifoaming agent, and the like, and these may be added appropriately as needed.

The carrier is classified into a solid carrier and a liquid carrier, and examples of the solid carrier include animal and plant powders such as starch, sugar, cellulose powder, cyclodextrin, activated carbon, soybean powder, wheat powder, rice husk powder, wood powder, fish powder, and milk powder; mineral powders such as talc, kaolin, bentonite, organic bentonite, calcium carbonate, calcium sulfate, sodium bicarbonate, zeolite, diatomaceous earth, white carbon, clay, alumina, silica, sulfur powder, and slaked lime; and the like. Examples of the liquid carrier include water; plant oils such as soybean oil and cotton seed oil; animal oils such as beef tallow and whale oil; alcohols such as ethyl alcohol and ethylene glycol; ketones such as acetone, methyl ethyl ketone, methyl isobutyl ketone, and isophorone; ethers such as dioxane and tetrahydrofuran; aliphatic hydrocarbons such as kerosene, lamp oil, liquid paraffin, and cyclohexane; aromatic hydrocarbons such as toluene, xylene, trimethylbenzene, tetramethylbenzene, and solvent naphtha; halogenated hydrocarbons such as chloroform and chlorobenzene; acid amides such as N,N-dimethylformamide; esters such as ethyl acetate ester and fatty acid glycerol ester; nitriles such as acetonitrile; sulfur-containing compounds such as dimethyl sulfoxide; N-methyl-2-pyrrolidone; and the like.

As the emulsifying agent, various emulsifying agents are used, and examples thereof include nonionic surfactants and anionic surfactants capable of functioning as an emulsifying agent, and the like.

Examples of the suspending agent include Veegum R (trade name, manufactured by Sanyo Chemical Industries, Ltd.), and the like.

Examples of the thickening agent include inorganic particles such as carbonates, silicates, oxides; organic substances such as urea-formaldehyde condensates; and the like.

Examples of the stabilizing agent include epoxidized animal and plant oils, nonionic polyoxyethylene surfactants, anionic polyoxyethylene surfactants, polyhydric alcohols, basic substances, and the like.

Examples of the dispersing agent include anionic surfactants such as naphthalene sulfonate salts, naphthalene sulfonate-formalin condensate salts, alkyl naphthalene sulfonate salts, alkyl naphthalene sulfonate-formalin condensate salts, phenol sulfonate salts, phenol sulfonate-formalin condensate salts, lignin sulfonate salts, polycarboxylate salts, polyoxyethylene alkyl ether sulfate ester salts, polyoxyethylene alkyl aryl ether sulfate salts, polyoxyethylene alkyl ether sulfate ester salts, polyoxyethylene alkyl ether phosphate salts, and polyoxyethylene alkyl aryl ether phosphate ester salts; nonionic surfactants such as oxyalkylene block polymers, polyoxyethylene alkyl ethers, polyoxyethylene alkyl aryl ethers, polyoxyethylene styryl aryl ethers, polyoxyethylene glycol alkyl ethers, polyoxyethylene hydrogenated castor oil, and polyoxyethylene castor oil; and the like.

Examples of the spreading agent include sodium alkyl sulfates, sodium alkylbenzene sulfonates, sodium lignin sulfonates, polyoxyethylene glycol alkyl ethers, polyoxyethylene lauryl ethers, polyoxyethylene alkyl aryl ethers, polyoxyethylene sorbitan fatty acid esters, and the like.

Examples of the wetting agent include cationic, anionic, amphoteric, and nonionic surfactants and the like as well known in this technical field.

Examples of the penetrating agent include fatty alcohol alkoxylates, mineral oils, plant oils, esters of mineral oils or plant oils, and the like.

Examples of the antifreezing agent include ethylene glycol, propylene glycol, and the like.

Examples of the antifoaming agent include Rhodorsil 432 (trade name, manufactured by Rhodia Nicca Ltd.), Antimousse (trade name, manufactured by BELCHIM CROP PROTECTION), and the like.

The blend ratio of the active ingredient of the invention and various auxiliary agents in weight ratio is about 1:100,000 to about 100,000:1, preferably about 1:1,000 to about 1,000:1.

For practically using these prepared products, the products may be used as they are or may be diluted with diluents such as water to given concentrations for use.

The control agent for soft rot in accordance with the invention may be mixed with other agrichemicals, fertilizers, and agents for reducing phytotoxicity for use or may be used in combination with them. In that case, far better effects or actions may sometimes be exerted. Other agrichemicals include for example herbicides, fungicides, antibiotics, phytohormone, insecticides, miticides, nematicides, and soil insecticides. Even without any specific description, these agrichemicals include salts, alkyl esters, hydrates, the agrichemicals in different crystal forms, and the agrichemicals in various structural isomers if any.

The active ingredients of the herbicides include those described below (under common names; some are under ISO applications).

(1) Those believed to exert herbicidal efficacy by disturbing hormone activities of plants, including phenoxy compounds such as 2,4-D, 2,4-D-butotyl, 2,4-D-butyl, 2,4-D-dimethylammonium, 2,4-D-diolamine, 2,4-D-ethyl, 2,4-D-2-ethylhexyl, 2,4-D-isobutyl, 2,4-D-isoctyl, 2,4-D-isopropyl, 2,4-D-isopropylammonium, 2,4-D-sodium, 2,4-D-isopropanol ammonium, 2,4-D-trolamine, 2,4-DB, 2,4-DB-butyl, 2,4-DB-dimethylammonium, 2,4-DB-isoctyl, 2,4-DB-potassium, 2,4-DB-sodium, dichlorprop, dichlorprop-butotyl, dichlorprop-dimethylammonium, dichlorprop-isoctyl, dichlorprop-potassium, dichlorprop-P, dichlorprop-P-dimethylammonium, dichlorprop-P-potassium, dichlorprop-P-sodium, MCPA, MCPA-butotyl, MCPA-dimethylammonium, MCPA-2-ethylhexyl, MCPA-potassium, MCPA-sodium, MCPA-thioethyl, MCPB, MCPB-ethyl, MCPB-sodium, mecoprop, mecoprop-butotyl, mecoprop-sodium, mecoprop-P, mecoprop-P-butotyl, mecoprop-P-dimethylammonium, mecoprop-P-2-ethylhexyl, mecoprop-P-potassium, naproanilide, and clomeprop; aromatic carboxylic acid compounds such as 2,3,6-TBA, dicamba, dicamba-butotyl, dicamba-diglycolamine, dicamba-dimethylammonium, dicamba-diolamine, dicamba-isopropylammonium, dicamba-potassium, dicambasodium, dichlobenil, picloram, picloram-dimethylammonium, picloram-isoctyl, picloram-potassium, picloram-triisopropanolammonium, picloram-trlisopropylammonium, picloram-trolamine, triclopyr, triclopyr-butotyl, triclopyr-triethylammonium, clopyralid, clopyralid-olamine, clopyralid-potassium, clopyralid-triisopropanolammonium and aminopyralid; and additional chemicals such as naptalam, naptalam-sodium, benazolin, benazolin-ethyl, quinclorac, quinmerac, diflufenzopyr, diflufenzopyr-sodium, fluroxypyr, fluroxypyr-2-butoxy-1-methylethyl, fluroxypyr-meptyl, chlorflurenol, and chlorflurenol-methyl.

(2) Those believed to exert herbicidal efficacy by inhibiting photosynthesis of plants, including urea compounds such as chlorotoluron, diuron, fluometuron, linuron, isoproturon, metobenzuron, tebuthiuron, dimefuron, isouron, karbutilate, methabenzthiazuron, metoxuron, monolinuron, neburon, siduron, terbumeton, and trietazine; triazine compounds such as simazine, atrazine, atratone, simetryn, prometryn, dimethametryn, hexazinone, metribuzin, terbuthylazine, cyanazine, ametryn, cybutryne, triaziflam, terbutryn, propazine, metamitron, prometon, and indaziflam; uracil compounds such as bromacil, bromacil-lithium, lenacil, and terbacil; anilide compounds such as propanil and cypromid; carbamate compounds such as swep, desmedipham, and phenmedipham; hydroxybenzonitrile compounds such as bromoxynil, bromoxynil-octanoate, bromoxynil-heptanoate, ioxynil, ioxynil-octanoate, ioxynil-potassium, and ioxynil-sodium; and additional chemicals such as pyridate, bentazone, bentazone-sodium, amicarbazone, methazole, and pentanochlor.

(3) Those believed to convert to a free radical by itself in the plant body to generate active oxygen, thereby exhibiting a rapid herbicidal efficacy, including quaternary ammonium salt compounds such as paraquat and diquat.

(4) Those believed to exert herbicidal efficacy by inhibiting chlorophyll biosynthesis of plants to abnormally accumulate a photosensitizing peroxide substance in plant body, including diphenyl ether compounds such as nitrofen, chlomethoxyfen, bifenox, acifluorfen, acifluorfen-sodium, fomesafen, fomesafen-sodium, oxyfluorfen, lactofen, aclonifen, ethoxyfen-ethyl (HC-252), fluoroglycofen-ethyl, and fluoroglycofen; cyclic imide compounds such as chlorphthalim, flumioxazin, flumiclorac, flumiclorac-pentyl, cinidon-ethyl, and fluthiacet-methyl; and additional other chemicals such as oxadiargyl, oxadiazon, sulfentrazone, carfentrazone-ethyl, thidiazimin, pentoxazone, azafenidin, isopropazole, pyraflufen-ethyl, benzfendizone, butafenacil, saflufenacil, flupoxam, fluazolate, profluazol, pyraclonil, flufenpyr-ethyl and bencarbazone.

(5) Those believed to exert herbicidal efficacy characterized by bleaching actitivities by inhibiting chromogenesis of plants such as carotenoids, including pyridazinone compounds such as norflurazon, chloridazon, and metflurazon; pyrazole compounds such as pyrazolynate, pyrazoxyfen, benzofenap, topramezone (BAS-670H), and pyrasulfotole; and additional other chemicals such as amitrole, fluridone, flurtamone, diflufenican, methoxyphenone, clomazone, sulcotrione, mesotrione, tembotrione, tefuryltrione (AVH-301), isoxaflutole, difenzoquat, difenzoquat-metilsulfate, isoxachlortole, benzobicyclon, picolinafen and beflubutamid.

(6) Those believed to exert strong herbicidal efficacy specifically to the gramineous plants, including aryloxyphenoxypropionic acid compounds such as diclofop-methyl, diclofop, pyriphenop-sodium, fluazifop-butyl, fluazifop, fluazifop-P, fluazifop-P-butyl, haloxyfop-methyl, haloxyfop, haloxyfop-etotyl, haloxyfop-P, haloxyfop-P-methyl, quizalofop-ethyl, quizalofop-P, quizalofop-P-ethyl, quizalofop-P-tefuryl, cyhalofopbutyl, fenoxaprop-ethyl, fenoxaprop-P, fenoxaprop-P-ethyl, metamifop-propyl, metamifop, clodinafop-propargyl, clodinafop, and propaquizafop; cyclohexandione compounds such as alloxydim-sodium, alloxydim, clethodim, sethoxydim, tralkoxydim, butroxydim, tepraloxydim, profoxydim, and cycloxydim; and other chemicals such as flamprop-M-methyl, flamprop-M, and flamprop-M-isopropyl.

(7) Those believed to exert herbicidal efficacy by inhibiting an amimo acid biosynthesis of plants, including sulfonylurea compounds such as chlorimuron-ethyl, chlorimuron, sulfometuron-methyl, sulfometuron, primisulfuron-methyl, primisulfuron, bensulfuron-methyl, bensulfuron, chlorsulfuron, metsulfuron-methyl, metsulfuron, cinosulfuron, pyrazosulfuron-ethyl, pyrazosulfuron, azimsulfuron, flazasulfuron, rimsulfuron, nicosulfuron, imazosulfuron, cyclosulfamuron, prosulfuron, flupyrsulfuron-methyl-sodium, flupyrsulfuron, triflusulfuron-methyl, triflusulfuron, halosulfuron-methyl, halosulfuron, thifensulfuron-methyl, thifensulfuron, ethoxysulfuron, oxasulfuron, ethametsulfuron, ethametsulfuron-methyl, iodosulfuron, iodosulfuron-methyl-sodium, sulfosulfuron, triasulfuron, tribenuron-methyl, tribenuron, tritosulfuron, foramsulfuron, trifloxysulfuron, trifloxysulfuron-sodium, mesosulfuronmethyl, mesosulfuron, orthosulfamuron, flucetosulfuron, amidosulfuron, propyrisulfuron (TH-547), NC-620, and the compounds described in International Publication WO2005092104; triazolopyrimidine sulfonamide compounds such as flumetsulam, metosulam, diclosulam, cloransulam-methyl, florasulam, penoxsulam, and pyroxsulam; imidazolinone compounds such as imazapyr, imazapyr-isopropyl ammonium, imazethapyr, imazethapyr-ammonium, imazaquin, imazaquin-ammonium, imazamox, imazamox-ammonium, imazamethabenz, imazamethabenz-methyl, and imazapic; pyrimidinylsalicylic acid compounds such as pyrithiobac-sodium, bispyribac-sodium, pyriminobac-methyl, pyribenzoxim, pyriftalid, and pyrimisulfan (KUH-021); sulfonylaminocarbonyltriazolinone compounds such as flucarbazone, flucarbazone-sodium, propoxycarbazone-sodium, and propoxycarbazone; and other chemicals such as glyphosate, glyphosate-sodium, glyphosate-potassium, glyphosate-ammonium, glyphosate-diammonium, glyphosate-isopropylammonium, glyphosate-trimesium, glyphosate-sesquisodium, glufosinate, glufosinate-ammonium, glufosinate-P, glufosinate-P-ammonium, glufosinate-P-sodium, bilanafos, bilanafos-sodium, and cinmethylin.

(8) Those believed to exert herbicidal efficacy by inhibiting cell mitosis of plants, including dinitroaniline compounds such as trifluralin, oryzalin, nitralin, pendimethalin, ethalfluralin, benfluralin, prodiamine, butralin, and dinitramine; amide compounds such as bensulide, napropamide, propyzamide, and pronamide; organic phosphorus compounds such as amiprofos-methyl, butamifos, anilofos, and piperophos; phenylcarbamate compounds such as propham, chlorpropham, barban, and carbetamide; cumylamine compounds such as daimuron, cumyluron, bromobutide, and methyldymron; other chemicals such as asulam, asulam-sodium, dithiopyr, thiazopyr, chlorthal-dimethyl, chlorthal, and diphenamid.

(9) Those believed to exert herbicidal efficacy by inhibiting protein biosynthesis or lipid biosynthesis of plants, including chloroacetamide compounds such as alachlor, metazachlor, butachlor, pretilachlor, metolachlor, S-metolachlor, thenylchlor, pethoxamid, acetochlor, propachlor, dimethenamid; dimethenamid-P, propisochlor, and dimethachlor; thiocarbamate compounds such as molinate, dimepiperate, pyributicarb, EPTC, butylate, vernolate, pebulate, cycloate, prosulfocarb, esprocarb, thiobencarb, diallate, tri-allate, and orbencarb; other chemicals such as etobenzanid, mefenacet, flufenacet, tridiphane, cafenstrole, fentrazamide, oxaziclomefone, indanofan, benfuresate, pyroxasulfone (KIH-485), dalapon, dalapon-sodium, TCA-sodium, and trichloroacetic acid.

(10) Those believed to exert herbicidal efficacy by being parasitic on plants, such as *Xanthomonas campestris, Epicoccosirus nematosorus, Epicoccosirus nematosperus, Exserohilum monoseras,* and *Drechsrela monoceras.*

(11) Those believed to exert herbicidal efficacy and not listed in (1) to (10), such as MSMA, DSMA, CMA, endothall, endothall-dipotassium, endothall-sodium, endothall-mono (N,N-dimethylalkylammonium), ethofumesate, sodium chlorate, pelargonic acid (nonanoic acid), fosamine, fosamine-ammonium, pinoxaden, ipfencarbazone (HOK-201), aclolein, ammonium sulfamate, borax, chloroacetic acid, sodium chloroacetate, cyanamide, methylarsonic acid, dimethylarsonic acid, sodium dimethy-larsinate, dinoterb, dinoterb-ammonium, dinoterb-diolamine, dinoterb-acetate, DNOC, ferrous sulfate, flupropanate, flupropanate-sodium, isoxaben, mefluidide, mefluidide-diolamine, metam, metam-ammonium, metam-potassium, metam-sodium, methyl isothiocyanate, pentachlorophenol, sodium pentachlorophenoxide, pentachlorophenol laurate, quinoclamine, sulfuric acid and urea sulfate.

The compound as the active ingredient of the fungicide (under the common name; some compounds under application are also included: or under the test code according to the Japan Plant Protection Association) includes for example triazolopyrimidine compounds such as 5-chloro-6-(2,4,6-trifluorophenyl) 7 (4-methylpiperidin-1-yl)[1,2,4]triazolo[1,5-a]pyrimidine; pyridinamine compounds such as fluazinam;
quinoxaline compounds such as quinomethionate;
dithiocarbamate compounds such as maneb, zineb, mancozeb, polycarbamate, metiram, propineb, and thiram;
cyanoacetamide compounds such as cymoxanil;
phenylamide compounds such as metalaxyl, metalaxyl-M, mefenoxam, oxadixyl, ofurace, benalaxyl, benalaxyl-M (kiralaxyl or chiralaxyl under the other name), furalaxyl, and cyprofuram;
sulfenic acid compounds such as dichlofluanid;
copper compounds including inorganic copper such as cupric hydroxide and oxine copper; isoxazole compounds such as hymexazol;
organic phosphorus compounds such as fosetyl-Al, tolclofos-methyl, S-benzyl O,O-diisopropylphosphorothioate, O-ethyl S,S-diphenylphosphorodithioate, aluminium ethylhydrogen phosphonate, edifenphos, and iprobenfos;
N-halogenothioalkyl compounds such as captan, captafol, and folpet;
benzanilide compounds such as flutolanil, mepronil, zoxamide, and tiadinil;
piperazine compounds such as triforine;
pyridine compounds such as pyrifenox;
carbinol compounds such as fenarimol and flutriafol;
piperidine compounds such as fenpropidin;
morpholine compounds such as fenpropimorph, spiroxamine, and tridemorph;
organic tin compounds such as fentin hydroxide and fentin acetate;
urea compounds such as pencycuron;
phenylcarbamate compounds such as diethofencarb;
oxazolidinone compounds such as famoxadone;
thiazole carboxamide compounds such as ethaboxam;
silylamide compounds such as silthiopham;
amino acid amide carbamate compounds such as iprovalicarb, benthiavalicarb-isopropyl, methyl N-(isopropoxycarbonyl)-L-valyl-(3RS)-3-(4-chlorophenyl)-beta-alaninate (valiphenalate);
imidazolidine compounds such as fenamidone;
hydroxyanilide compounds such as fenhexamid;
oxime ether compounds such as cyflufenamid;
phenoxyamide compounds such as fenoxanil;
anthraquinone compounds;
crotonic acid compounds;
4-quinolinol derivative compounds such as 2,3-dimethyl-6-t-butyl-8-fluoro-4-acetylquinoline;
cyanomethylene compounds such as 2-(2-fluoro-5-(trifluoromethyl)phenylthio)-2-(3-(2-methoxyphenyl)thiazolidin-2-ylidene)acetonitrile;
and other compounds such as pyribencarb, isoprothiolane, pyroquilon, diclomezine, quinoxyfen, propamocarb hydrochloride, chloropicrin, dazomet, metam-sodium, nicobifen, metrafenone, UBF-307, diclocymet, proquinazid, mandipropamid, fluopicolide, carpropamid, meptyldinocap, 6-t-butyl-8-fluoro-2,3-dimethylquinolin-4-yl acetate, 3-(2,3,4-trimethoxy-6-methylbenzoyl)-5-chloro-2-methoxy-4-methylpyridine, 4-(2,3,4-trimethoxy-6-methylbenzoyl)-2,5-dichloro-3-trifluoromethylpyridine, 4-(2,3,4-trimethoxy-6-methylbenzoyl)-2-chloro-3-trifluoromethyl-5-methoxypyridine, N-[(3',4'-dichloro-1,1-dimethyl)phenacyl]-3-trifluoromethyl-2-pyridine carboxamide, N-[(3',4'-dichloro-1,1-dimethyl)phenacyl]-3-methyl-2-thiophen carboxamide, N-[(3',4'-dichloro-1,1-dimethyl)phenacyl]-1-methyl-3-trifluoromethyl-4-pyrazole carboxamide, N-[[2'-methyl-4'-(2-propyloxy)-1,1-dimethyl]phenacyl]-3-trifluoromethyl-2-pyridine carboxamide, N-[[2'-methyl-4'-(2-propyloxy)-1,1-dimethyl]phenacyl]-3-methyl-2-thiophen carboxamide, N-[[2'-methyl-4'-(2-propyloxy)-1,1-dimethyl]phenacyl]-1-methyl-3-trifluoromethyl-4-pyrazole carboxamide, N-[[4'-(2-propyloxy)-1,1-dimethyl]phenacyl]-3-trifluoromethyl-2-pyridine carboxamide, N-[[4'-(2-propyloxy)-1,1-dimethyl]phenacyl]-3-methyl-2-thiophen carboxamide, N-[[4'-(2-propyloxy)-1,1-dimethyl]phenacyl]-1-methyl-3-trifluoromethyl-4-pyrazole carboxamide, N-[[2'-methyl-4'-(2-pentyloxy)-1,1-dimethyl]phenacyl]-3-trifluoromethyl-2-pyridine carboxamide, N-[[4'-(2-pentyloxy)-1,1-dimethyl]phenacyl]-3-trifluoromethyl-2-pyridine carboxamide, S-2188 (fenpyrazamine), ZF-9646, BCF-051, BCM-061 and BCM-062.

The antibiotics include for example streptomycin, validamycin, kasugamycin, polyoxins, avermectin, emamectin benzoate, milbemectin, milbemycin, spinosad, ivermectin, lepimectin, DE-175, abamectin, emamectin, and spinetoram.

The phytohormone includes for example auxin, gibberellin, cytokinin, abscisic acid, ethylene, brassinosteroid, jasmonic acid, florigen, strigolactone, and salicylic acid.

The compound (under the common name; some compounds are under application or by the test code) as the active ingredient of the insecticides, the miticides, the nematicides, or the soil insecticides includes for example organic phosphate ester compounds such as profenofos, dichlorvos, fenamiphos, fenitrothion, EPN, diazinon, chlorpyrifos, chlorpyrifos-methyl, acephate, prothiofos, fosthiazate, cadusafos, disulfoton, isoxathion, isofenphos, ethion, etrimfos, quinalphos, dimethylvinphos, dimethoate, sulprofos, thiometon, vamidothion, pyraclofos, pyridaphenthion, pirimiphos-methyl, propaphos, phosalone, formothion, malathion, tetrachlorvinphos, chlorfenvinphos, cyanophos, trichlorfon, methidathion, phenthoate, ESP, azinphos-methyl, fenthion, heptenophos, methoxychlor, parathion, phosphocarb, demeton-S-methyl, monocrotophos, methamidophos, imicyafos, parathion-methyl, terbufos, phosphamidon, phosmet, and phorate;
carbamate compounds such as carbaryl, propoxur, aldicarb, carbofuran, thiodicarb, methomyl, oxamyl, ethiofencarb, pirimicarb, fenobucarb, carbosulfan, benfuracarb, bendiocarb, furathiocarb, isoprocarb, metolcarb, xylylcarb, XMC, and fenothiocarb;
nereistoxin derivatives such as cartap, thiocyclam, bensultap, and thiosultap-sodium;
organic chlorine compounds such as dicofol, tetradifon, endosulfan, dienochlor, and dieldrin;
organic metal compounds such as fenbutatin oxide, and cyhexatin;
pyrethroid compounds such as fenvalerate, permethrin, cypermethrin, deltamethrin, cyhalothrin, tefluthrin, ethofenprox, flufenprox, cyfluthrin, fenpropathrin, flucythrinate, fluvalinate, cycloprothrin, lambda-cyhalothrin, pyrethrin, esfenvalerate, tetramethrin, resmethrin, protrifenbute, bifenthrin, zeta-cypermethrin, acrinathrin, alpha-cypermethrin, allethrin, gamma-cyhalothrin, theta-cypermethrin, tau-fluvalinate, tralomethrin, profluthrin, beta-cypermethrin, beta-cyfluthrin, metofluthrin, phenothrin, imidate, and flumethrin;
benzoylurea compounds such as diflubenzuron, chlorfluazuron, teflubenzuron, flufenoxuron, lufenuron, novaluron, triflumuron, hexaflumuron, bistrifluron, noviflumuron, and fluazuron;
benzoylurea compounds such as diflubenzuron, chlorfluazuron, teflubenzuron, flufenoxuron, lufenuron, novaluron, triflumuron, hexaflumuron, bistrifluron, noviflumuron and fluazuron;
juvenile hormone-like compounds such as methoprene, pyriproxyfen, fenoxycarb, and diofenolan;
pyridazinone compounds such as pyridaben;
pyrazole compounds such as fenpyroximate, fipronil, tebufenpyrad, ethiprole, tolfenpyrad, acetoprole, pyrafluprole and pyriprole;
neonicotinoid such as imidacloprid, nitenpyram, acetamiprid, thiacloprid, thiamethoxam, clothianidin, nidinotefuran, and dinotefuran;
hydrazine compounds such as tebufenozide, methoxyfenozide, chromafenozide, and halofenozide;
pyridine compounds such as pyridaryl, and flonicamid;
tetronic acid compounds such as spirodiclofen;
strobilurin compounds such as fluacrypyrim;
pyridinamine compounds such as flufenerim;
dinitro compounds, organic sulfur compounds, urea compounds, triazine compounds, hydrazone compounds, and other compounds, such as buprofezin, hexythiazox, amitraz, chlordimeform, silafluofen, triazamate, pymetrozine, pyrimidifen, chlorfenapyr, indoxacarb, acequinocyl, etoxazole, cyromazine, 1,3-dichloropropene, diafenthiuron, benclothiaz, bifenazate, spiromesifen, spirotetramat, propargite, clofentezine, metaflumizone, flubendiamide, cyflumetofen, chlorantraniliprole, cyenopyrafen, pyrifluquinazone, fenazaquin, pyridaben, amidoflumet, chlorobenzoate, sulfluramid, hydramethylnon, metaldehyde, HGW-86, ryanodine, flufenerim, pyridalyl, spirodiclofen, verbutin, thiazolylcinnanonitrile, and amidoflumet; and AKD-1022, and IKA-2000. Further, the other examples of the compound as the active ingredient of the insecticides, the miticides, the nematicides, or the soil insecticides include microbial agrichemicals such as crystalline protein toxins which is generated by *Bacillus thuringiensis aizawai, Bacillus thuringiensis kurstaki, Bacillus thuringiensis israelensis, Bacillus thuringiensis japonensis, Bacillus thuringiensis tenebrionis* and *Bacillus thuringiensis*, and insect pathogenic virus agent, insect pathogenic filamentous fungi agent, and nematoda pathogenic filamentous fungi agent; natural products such as azadirachtin and rotenone; and repellants such as deet.

The fertilizer includes for example liquid fertilizers, vitalizing agents, active agents and liquid fertilizers for leaves.

The agents for reducing phytotoxicity include for example calcium carbonate agent.

Furthermore, the blend ratio in weight ratio of the active ingredient of the invention and other agrichemicals is about 1:10,000 to about 10,000:1, preferably about 1:1,000 to about 1,000:1.

Furthermore, the blend ratio in weight ratio of the active ingredient of the invention and fertilizers is about 1:100,000 to about 100,000:1, preferably about 1:1,000 to about 1,000:1.

Additionally, the blend ratio in weight ratio of the active ingredient of the invention and agents for reducing phytotoxicity is about 1:100,000 to about 100,000:1, preferably about 1:1,000 to about 1,000:1.

These other agrichemicals, fertilizers, agents for reducing phytotoxicity and the like may be used singly or in combination of two types or more thereof. Additionally, the active ingredient of the invention and other agrichemicals, fertilizers, agents for reducing phytotoxicity and the like may separately be formulated and then mixed together for use; otherwise, these may be formulated together for use.

The application of the active ingredient of the invention as the control agent for soft rot in accordance with the invention to cultivation soil for plants is now described. Embodiments of individual application methods are for example described below.

1. The active ingredient is applied to cultivation soil for plants; an agricultural mulch-sheet is then spread; subsequently, seeds of a plant are sowed or seedlings of a plant are planted through the planting holes of the agricultural mulch-sheet.
2. An agricultural mulch-sheet is spread over cultivation soil for plants; planting holes to sow seeds of a plant or to plant seedlings of a plant are bored into the mulch-sheet, and then, the active ingredient is applied to the agricultural mulch-sheet, and thereafter, seeds of a plant are sowed or seedlings of a plant are planted through the planting holes.
3. The active ingredient is applied to cultivation soil for plants after sowing seeds of a plant or planting seedlings of a plant.
4. After the active ingredient is applied to cultivation soil for plants, seeds of a plant are sowed or seedlings of a plant are planted.

Preferably, the active ingredient is applied to the surface of cultivation soil according to the control methods described above in 1 to 4. More preferably, the active ingredient is applied to the surface of cultivation soil without mixing in cultivation soil.

As for the application of the control agent for soft rot of the invention to the soil, by using an appropriate apparatus such as a watering pot, a sprayer, a hand-operated granule applicator, an electric-powered granule applicator, or a powder applicator, for example, spraying, nebulizing, misting, atomizing, granule applying, or the like can be performed. Further, the control agent is sprayed onto soil in a cell tray, and planting of seedlings may be performed together with the soil in the cell.

Before or after the application of the control agent for soft rot in accordance with the invention on the soil, routine agricultural mulch-sheets such as mulch-film, functional mulch-film, agricultural polyethylene or biodegradable plastic-made mulch-film can be used.

According to the control method for soft rot in accordance with the invention, the amount of the active ingredient of the invention to be applied to cultivation soil should be adjusted to 0.025 to 2.5 g/m², preferably 0.05 to 1 g/m². The amount thereof to be applied to cultivation soil can appropriately be modified, depending on the form of the preparation, the application method, the plant to be a target for the application, the application timing, the site and the status of the occurrence of soft rot.

In the invention, examples of the plant to be a target for controlling soft rot include vegetables and the like. Examples of the vegetables include asparagus, endive, calla, cauliflower, cabbage, amorphophallus konjac, Brassica campestris, celery, Japanese radish, tobacco, onion, qing-geng-cai, tomato, eggplant, carrot, green onion, Chinese cabbage, Brassica oleracea×Brassica campestris, parsley, potato, broccoli, rakkyo, lettuce, wasabi, oil-seed rape, and the like.

EXAMPLES

Examples of the invention are now described together with comparative examples. However, the invention is never limited to these examples.

Example 1

(1) Preparation of Spray Solutions
1) Preparation of Azoxystrobin (Amistar 20 FLOWABLE)
200 g/l Azoxystrobin (Amistar 20 FLOWABLE [trade name], manufactured by Syngenta Japan K.K.) was adjusted to 250 g ai/10a (0.25 g/m², 1250 ml Product/10a) as the amount of the active ingredient and to 150 L/10a as the volume of diluent water.
2) Preparation of cyazofamid (RANMAN FLOWABLE)
100 g/l Cyazofamid (RANMAN FLOWABLE [trade name], manufactured by Ishihara Sangyo Kaisha, Ltd.) was adjusted to 250 g ai/10a (0.25 g/m², 2500 ml Product/10a) as the amount of the active ingredient and to 150 L/10a as the volume of diluent water.
3) Preparation of Amisulbrom (LEIMAY FLOWABLE)
177 g/l Amisulbrom (LEIMAY FLOWABLE [trade name], manufactured by Nissan Chemical Industries, Ltd.) was adjusted individually to 250 g ai/10a (0.25 g/m², 1412 ml Product/10a) as the amount of the active ingredient and to 150 L/10a as the volume of diluent water.
(2) Test for Controlling Diseases and Damages of Chinese Cabbage
After spreading an agricultural mulch-sheet and opening planting holes (diameter of about 9 cm) for permanent planting through the mulch-sheet, the spray solutions prepared as described above were sprayed onto the planting holes such that the amount of treated active ingredient of each spray solution was 0.25 g/m² (150 L per 10a), followed by air-drying; subsequently, seedlings of Chinese cabbage (cultivar: Muso) grown for 4 weeks in cell mold trays (128 holes/nursery box) were planted such that 30 seedlings were planted in each test lot having an area of 6 m² with two replications.

Comparative Example 1

(1) Preparation of Spray Solution
Preparation was performed by diluting streptomycin (Mycin 20 wettable powder solution [under the trade name] manufactured by Hokko Chemical Industry Co., Ltd.) with water to 1/1000.
(2) Test for Controlling Diseases and Damages of Chinese Cabbage
In a field spread with the agricultural mulch-sheet, Chinese cabbage seedlings (cultivar: Muso) grown by the same method as in Example 1 were planted by the same method as in Example 1, for spraying the spray solution of streptomycin prepared above in (1) (at each spray volume of 300 L/10a) three times (13 days, 20 days and and 27 days after the planting of the seedlings) on the stems and leaves.

54 days after the start of the tests, all the plants in each lot were examined about the severity level of the disease; according to the following equations, the ratio of the plants with the onset of the disease, the frequency of the disease, and the disease control value were calculated to determine and rank the effects at A to D levels. The results of these tests are shown in Table 1. Because soft rot is a disease with damages hardly controlled, herein, even a chemical at the level C determined by the tests of the effects can practically be used.

Ratio of the plants with the onset of the disease=(Number of plants with the onset of the disease/number of plants examined)*100

Frequency of the disease=[sigma(number of plants with the onset of the disease at each severity level*index of the onset of the disease)/(plants examined*4)]*100

Disease control value=[1−(frequency of the disease in the treated lot/frequency of the disease in the non-treated lot)]*100

Herein, the standard for assessing the index of the onset of the disease is as follows.

INDEX OF THE ONSET OF THE DISEASE

0: No onset
1: Onset in some of outer leaves (shippable)
2: Onset in outer leaves and some of head leaves (by removing damaged parts, the resulting cabbage can be shipped as small cabbage but is ranked as grade B).
3: Most of head leaves are inflicted with the onset of the disease or with severer damages (not shippable)
4: Whole cabbage plant is inflicted with the onset of the disease and is dead.

DETERMINATION OF EFFECTS

A: Highly effective (61 or larger disease control value)
B: Effective (41 to 60 disease control value)
C: Effective at low level (21 to 40 disease control value)
D: Poorly effective (20 or smaller disease control value)

TABLE 1

| Active ingredient | Amount of active ingredient or dilution ratio | Determination of effect |
|---|---|---|
| Azoxystrobin (Amistar-20 FL) | 250 g ai/10 a 150 L/10 a | C |
| Cyazofamid (RANMAN FL) | 250 g ai/10 a 150 L/10 a | D |
| Amisulbrom (LEIMAY FL) | 250 g ai/10 a 150 L/10 a | C |
| Streptomycin | 1/1000 dilution | D |

The onset of the disease in the non-treated lot in Table 1 was tested under conditions for moderate frequency where the mean level of the frequency of the disease was 45.0. The control effect of streptomycin sprayed on the stems and leaves was at the level D (poorly effective), but the control effects of azoxystrobin and amisulbrom were at the level C (effective at low level). Hence, it was confirmed that the control effects thereof were higher than that of streptomycin as a control agent for soft rot, suggesting that azoxystrobin and amisulbrom were effective against soft rot of Chinese cabbage. While the control effect of cyazofamid was at the level D (poorly effective), the effect was at the same level as that of streptomycin, suggesting that cyazofamid was also effective for controlling soft rot of Chinese cabbage.

Example 2

(1) Preparation of Spray Solutions
1) Preparation of Azoxystrobin (Amistar 20 FLOWABLE)
200 g/l Azoxystrobin (Amistar 20 FLOWABLE [trade name], manufactured by Syngenta Japan K.K.) was adjusted to 500 g ai/10a (0.5 g/m$^2$, 2500 ml Product/10a) as the amount of the active ingredient and to 150 L/10a as the volume of diluent water.
2) Preparation of Triflumizol (TRIFUMIN WP)
30% w/w triflumizol (TRIFUMIN WP [trade name], manufactured by Nippon Soda Co., Ltd.) was adjusted to 500 g ai/10a (0.5 g/m$^2$, 1667 g Product/10a) as the amount of the active ingredient and to 150 L/10a as the volume of diluent water.
3) Preparation of Cyazofamid (RANMAN PLOWABLE)
100 g/l cyazofamid (RANMAN PLOWABLE [trade name], manufactured by Ishihara Sangyo Kaisha, Ltd.) was adjusted to 500 g ai/10a (0.5 g/m$^2$, 5000 ml Product/10a) as the amount of the active ingredient and to 150 L/10a as the volume of diluent water.
4) Preparation of Penthiopyrad (GAIA WG)
50% w/w penthiopyrad (GAIA WG [trade name], manufactured by Mitsui Chemicals Agro, Inc.) was adjusted to 500 g ai/10a (0.5 g/m$^2$, 1000 g Product/10a) as the amount of the active ingredient and to 150 L/10a as the volume of diluent water.
5) Preparation of Flusulfamide (SCABLOCK SC)
50 g/l flusulfamide (SCABLOCK SC [trade name], manufactured by Mitsui Chemicals Agro, Inc.) was adjusted to 500 g ai/10a (0.5 g/m$^2$, 10000 ml Product/10a) as the amount of the active ingredient and to 150 L/10a as the volume of diluent water.
6) Preparation of Chlorothalonil (Daconil 1000)
400 g/l chlorothalonil (Daconil 1000 [the trade name], manufactured by Sumitomo Chemical, Limited) was adjusted to 1000 g ai/10a (1.0 g/m$^2$, 2500 ml Product/10a) as the amount of the active ingredient and to 150 L/10a as the volume of diluent water.
(2) Test for Controlling Diseases and Damages of Chinese Cabbage
After spreading an agricultural mulch-sheet and opening planting holes (diameter of about 5 cm) for permanent planting through the mulch-sheet, the spray solutions prepared as described above were sprayed onto the planting holes such that the amount of treated active ingredient of chlorothalonil was 1.0 g/m$^2$ (150 L per 10a) and the amount of each of the remaining spray solutions was 0.5 g/m$^2$ (150 L per 10a), followed by air-drying; subsequently, seedlings of Chinese cabbage (cultivar Harebutai 65) grown for 4 weeks in cell mold trays (128 holes/nursery box) were planted such that 19 seedlings were planted in each test lot having an area of 2.4 m$^2$ with two replications.

Comparative Example 2

(1) Preparation of Spray Solution
Preparation was performed by diluting streptomycin (Mycin 20 wettable powder solution [under the trade name] manufactured by Hokko Chemical Industry Co., Ltd.) with water to 1/1000.

(2) Test for controlling diseases and damages of Chinese cabbage
In a field spread with the agricultural mulch-sheet, Chinese cabbage seedlings (cultivar: Harebutai 65) grown by the same method as in Example 2 were planted by the same method as in Example 2, for spraying the spray solution of streptomycin prepared above in (1) (at each spray volume of 300 L/10a) twice (27 days and 48 days after the planting of the seedlings) on the stems and leaves with a sprayer.
64 days after the start of the tests, all the plants in each lot were examined about the severity level of the disease to assess the frequency of the disease and the disease control value. In the same manner as described above, the frequency of the disease and the disease control value were determined. The results of these tests are shown in Table 2. Additionally, soft rot is a disease with damages hardly controlled, so even a chemical at the level C determined by the tests of the effects can practically be used.

TABLE 2

| Active ingredient | Amount of active ingredient or dilution ratio | Determination of effect |
| --- | --- | --- |
| Azoxystrobin (Amistar-20 FL) | 500 g ai/10 a 150 L/10 a | B |
| Triflumizol (TRIFUMIN WP) | 500 g ai/10 a 150 L/10 a | C |
| Cyazofamid (RANMAN FL) | 500 g ai/10 a 150 L/10 a | C |
| Penthiopyrad (GAIA WG) | 500 g ai/10 a 150 L/10 a | C |
| Flusulfamide (SCABLOCK SC) | 500 g ai/10 a 150 L/10 a | B |
| Chlorothalonil (Daconil 1000) | 1000 g ai/10 a 150 L/10 a | B |
| Streptomycin | 1/1000 dilution | B |

The onset of the disease in the non-treated lot in Table 2 was tested under conditions for moderate frequency where the mean level of the frequency of the disease was 31.6. The control effects of azoxystrobin, flusulfamide, and chlorothalonil were determined as the level B, similar to the level of the cabbage sprayed with streptomycin on its stems and leaves, suggesting that azoxystrobin, flusulfamide and chlorothalonil were effective against soft rot of Chinese cabbage. The control effects of triflumizol, cyazofamid and penthiopyrad were at the level C (effective at a low level), suggesting that these chemicals were also effective for controlling soft rot of Chinese cabbage.

Reference Test Example 1

Inhibition Test of Growth of Bacteria Causing Soft Rot of Potato

An inhibition test of the growth of bacteria causing the soft rot was done, when a control agent was directly applied to the bacteria causing the soft rot. A given volume of each pesticide of cyazofamid (RANMAN 400SC [trade name] manufactured by Ishihara Sangyo Kaisha, Ltd.), amisulbrom (LEIMAY FLOWABLE [trade name], manufactured by Nissan Chemical Industries, Ltd.) and streptomycin (Mycin Wettable powder [trade name] manufactured by Hokko Chemical Industry Co., Ltd.) was added together with a suspension of the bacteria causing the soft rot (*Erwinia carotovora*) to a preliminarily dissolved PSA culture medium (55 degrees Celsius) for subsequent thorough agitation, which was then spread on a plate for culturing at 25 degrees Celsius for 4 days, to examine the growth state. Subsequently, the formed colonies were examined according to the following three grades.

+: at the same level as the level of non-treated lot.

Plus or minus: apparently less than the colonies of the non-treated lot.

−: almost no colonies observed. The results of these tests are shown in Table 3.

TABLE 3

| Active ingredient | Concentration of active ingredient (ppm) | | |
|---|---|---|---|
| | 1000 | 500 | 100 |
| Cyazofamid (RANMAN 400SC) | +, + | +, + | +, + |
| Amisulbrom (LEIMAY FL) | +, + | +, + | +, + |
| Streptomycin | 10 −, − | 1 −, − | |

Table 3 shows that cyazofamid and amisulbrom treated at an active ingredient concentration of 1,000 ppm against *Erwinia carotovora* never inhibited the growth, suggesting that the compounds had no direct antibacterial activity against *Erwinia carotovora*. In contrast, the antibiotic streptomycin at an active ingredient concentration of 1 ppm exerted a direct antibacterial activity against *Erwinia carotovora*.

Reference Test Example 2

Inhibition Test of Growth of Bacteria Causing Soft Rot of Potato

An inhibition test of the growth of bacteria causing the soft rot was done, when a control agent was directly applied to the bacteria causing the soft rot. A given volume of each pesticide of azoxystrobin (Amistar-20 FLOWABLE [trade name], manufactured by Syngenta Japan K.K.), penthiopyrad (GAIA WG [trade name], manufactured by Mitsui Chemicals Agro, Inc.), flusulfamide (SCABLOCK SC [trade name] manufactured by Mitsui Chemicals Agro, Inc.), and streptomycin (Mycin Wettable powder [trade name] manufactured by Hokko Chemical Industry Co., Ltd.) was added together with a suspension of the bacteria causing the soft rot (*Erwinia carotovora*) to a preliminarily dissolved PSA culture medium (55 degrees Celsius) for subsequent thorough agitation, which was then spread on a plate for culturing at 27 degrees Celsius for 2 days, to examine the growth state. Subsequently, the formed colonies were examined according to the following three grades.

+: at the same level as the level of non-treated lot.

Plus or minus: apparently less than the colonies of the non-treated lot.

−: almost no colonies observed.

The results of these tests are shown in Table 4.

TABLE 4

| Active ingredient | Concentration of active ingredient (ppm) | | |
|---|---|---|---|
| | 1000 | 500 | 100 |
| Azoxystrobin (Amistar-20 FL) | +, + | +, + | +, + |
| Penthiopyrad (GAIA WG) | +, + | +, + | +, + |

TABLE 4-continued

| Active ingredient | Concentration of active ingredient (ppm) | | |
|---|---|---|---|
| | 1000 | 500 | 100 |
| Flusulfamide (SCABLOCK SC) | +, + | +, + | +, + |
| Streptomycin | 10 −, − | 1 −, − | |

Table 4 shows that azoxystrobin, penthiopyrad and flusulfamide treated at an active ingredient concentration of 1,000 ppm against *Erwinia carotovora* never inhibited the growth, suggesting that the compounds had no direct antibacterial activity against *Erwinia carotovora*. In contrast, the antibiotic streptomycin at an active ingredient concentration of 1 ppm exerted a direct antibacterial activity against *Erwinia carotovora*.

Reference Test Example 3

Inhibition Test of Growth of Bacteria Causing Soft Rot of Potato

An inhibition test of the growth of bacteria causing the soft rot was done, when a control agent was directly applied to the bacteria causing the soft rot. A given volume of each pesticide of triflumizol (TRIFUMIN WP [trade name] manufactured by Nippon Soda Co., Ltd.), chlorothalonil (Daconil 1000 [trade name], manufactured by Sumitomo Chemical Company, Limited) and streptomycin (Mycin Wettable powder [trade name] manufactured by Hokko Chemical Industry Co., Ltd.) was added together with a suspension of the bacteria causing the soft rot (*Erwinia carotovora*) to a preliminarily dissolved PSA culture medium (55 degrees Celsius) for subsequent thorough agitation, which was then spread on a plate for culturing at 27 degrees Celsius for 2 days, to examine the growth state. Subsequently, the formed colonies were examined according to the following three grades.

+: at the same level as the level of non-treated lot.

Plus or minus: apparently less than the colonies of the non-treated lot.

−: almost no colonies observed.

The results of these tests are shown in Table 5.

TABLE 5

| Active ingredient | Concentration of active ingredient (ppm) | | |
|---|---|---|---|
| | 1000 | 500 | 100 |
| Triflumizol (TRIFUMIN WP) | +, + | +, + | +, + |
| Chlorothalonil (Daconil 1000) | +, + | +, + | +, + |
| Streptomycin | 10 −, − | 1 +, ± | |

Table 5 shows that triflumizol and chlorothalonil treated at an active ingredient concentration of 1,000 ppm against *Erwinia carotovora* never inhibited the growth, suggesting that the compounds had no direct antibacterial activity against *Erwinia carotovora*. In contrast, the antibiotic streptomycin at an active ingredient concentration of 10 ppm exerted a direct antibacterial activity against *Erwinia carotovora*.

Example 3

(1) Preparation of Spray Solutions
1) Preparation of Kresoxim-Methyl (STROBY FLOWABLE)

442 g/l kresoxim-methyl (STROBY FLOWABLE [trade name], manufactured by BASF) was adjusted to 500 g ai/10a (0.5 g/m$^2$, 1131 ml Product/10a) as the amount of the active ingredient and to 150 L/10a as the volume of diluent water.
2) Preparation of Iminoctadine Albesilate Salt (BELLKUTE FLOWABLE) 300 g/l iminoctadine albesilate salt (BELLKUTE FLOWABLE [trade name], manufactured by Nippon Soda Co., Ltd.) was adjusted to 500 g ai/10a (0.5 g/m$^2$, 1667 ml Product/10a) as the amount of the active ingredient and to 150 L/10a as the volume of diluent water.
water.
(2) Test for controlling diseases and damages of Chinese cabbage After spreading an agricultural mulch-sheet and opening planting holes (diameter of about 9 cm) for permanent planting through the mulch-sheet, the spray solutions prepared as described above were sprayed onto the planting holes such that the amount of treated active ingredient of each spray solution was 0.5 g/m$^2$ (150 L per 10a), followed by air-drying; subsequently, seedlings of Chinese cabbage (cultivar: Muso) grown for 4 weeks in cell mold trays (128 holes/nursery box) were planted such that 30 seedlings were planted in each test lot having an area of 6 m$^2$ with two replications.

Comparative Example 3

(1) Preparation of Spray Solution

Preparation was performed by diluting a chemical solution (Agrimycin WP100 [trade name] manufactured by Pfizer) containing oxytetracycline at 1.5% and streptomycin sulfate salt at 18.8% with water to 1/1500.
(2) Test for Controlling Diseases and Damages of Chinese Cabbage In a field spread with the agricultural mulch-sheet, Chinese cabbage seedlings (cultivar: Muso) grown by the same method as in Example 3 were planted by the same method as in Example 3, for spraying the spray solution prepared above in (1) (at each spray volume of 300 L/10a) three times (21 days, 30 days and 39 days after the planting of the seedlings) on the stems and leaves.

51 days after the start of the tests, all the plants in each lot were examined about the severity level of the disease to assess the frequency of the disease and the disease control value. The frequency of the disease and the disease control value were determined in the same manner as described above. The results of these tests are shown in Table 6. Because soft rot is a disease with damages hardly controlled, herein, even a chemical at the level C determined by the tests of the effects can practically be used.

TABLE 6

| Active ingredient (trade names) | Amount of active ingredient Spray volume | Determination of effect |
| --- | --- | --- |
| Kresoxim-methyl (STROBY FL) | 500 g ai/10 a 150 L/10 a | C |
| Iminoctadine albesilate salt (BELLKUTE FL) | 500 g ai/10 a 150 L/10 a | B |
| Oxytetracycline + streptomycin sulfate salt (Agrimycin WP) | 1/1500 300 L/10 a | D |

The onset of the disease in the non-treated lot in Table 6 was tested under conditions of very high frequency where the mean level of the frequency of the disease was 84.6. The control effect of Agrimycin WP sprayed on the stems and leaves was at the level D (poorly effective), but the control effects of kresoxim-methyl and iminoctadine albesilate salt were at the level C (effective at low level) and B (effective), respectively. Hence, it was confirmed that the control effects thereof were higher than that of streptomycin as a control agent for soft rot, suggesting that kresoxim-methyl and iminoctadine albesilate salt were effective against soft rot of Chinese cabbage.

Example 4

(1) Preparation of Spray Solutions
1) Preparation of Kresoxim-Methyl (STROBY FLOWABLE)

442 g/lkresoxim-methyl (STROBY FLOWABLE [trade name], manufactured by BASF) was adjusted to 500 g ai/10a (0.5 g/m$^2$, 1131 ml Product/10a) as the amount of the active ingredient and to 150 L/10a as the volume of diluent water.
2) Preparation of Thiophanate Methyl (Topsin M WP)

70% w/w thiophanate methyl (Topsin M WF [trade name], manufactured by Nippon Soda Co., Ltd.) was adjusted to 1000 g ai/10a (1 g/m$^2$, 1429 g Product/10a) as the amount of the active ingredient and to 150 L/10a as the volume of diluent water.
3) Preparation of Boscalid (Cantus DF)

50% w/w boscalid (Cantus DF [trade name], manufactured by BASF) was adjusted to 500 g ai/10a (0.5 g/m$^2$; 1000 g Product/10a) as the amount of the active ingredient and to 150 L/10a as the volume of diluent water.
4) Preparation of Procymidone (Sumilex WP)

50% w/w procymidone (Sumilex WP [trade name], manufactured by Sumitomo Chemical Agro) was adjusted to 500 g ai/10a (0.5 g/m$^2$, 1000 g Product/10a) as the amount of the active ingredient and to 150 L/10a as the volume of diluent water.
5) Preparation of Iprodione (Rovral 500 Aqua)

400 g/l iprodione (Rovral 500 Aqua [trade name], manufactured by Bayer Crop Science Co., Ltd.) was adjusted to 500 g ai/10a (0.5 g/m$^2$, 1250 nil Product/10a) as the amount of the active ingredient and to 150 L/10a as the volume of diluent water.
6) Preparation of Fludioxonil (Seibia FLOWABLE)

200 g/l fludioxonil (Seibia FLOWABLE [trade name], manufactured by Syngenta Japan K.K.) was adjusted to 500 g ai/10a (0.5 g/m$^2$, 2500 ml Product/10a) as the amount of the active ingredient and to 150 L/10a as the volume of diluent water.
7) Preparation of Mepanipyrim (Flupika PLOWABLE)

400 g/l mepanipyrim (Flupika PLOWABLE [trade name], manufactured by Nippon Soda Co., Ltd.) was adjusted to 500 g ai/10a (0.5 g/m$^2$, 1250 ml Product/10a) as the amount of the active ingredient and to 150 L/10a as the volume of diluent water.
(2) Test for Controlling Diseases and Damages of Chinese Cabbage After spreading an agricultural mulch-sheet and opening planting holes (diameter of about 5 cm) for permanent planting through the mulch-sheet, the spray solutions prepared as described above were sprayed onto the planting holes such that the amount of treated active ingredient of each spray solution was 0.5 g/m$^2$ (150 L per 10a), followed by air-drying; subsequently, seedlings of Chinese cabbage (cultivar: Ouraku 60) grown for 4 weeks in cell mold trays (128 holes/nursery box) were planted such that 30 seedlings were planted in each test lot having an area of 2.5 m² with two replications.

Comparative Example 4

(1) Preparation of Spray Solution

Preparation was performed by diluting a chemical solution (Agrimycin WP100 [trade name] manufactured by Pfizer) containing oxytetracycline at 1.5% and streptomycin sulfate salt at 18.8% with water to 1/1500.

(2) Test for Controlling Diseases and Damages of Chinese Cabbage

In a field spread with the agricultural mulch-sheet, Chinese cabbage seedlings (cultivar: Ouraku 60) grown by the same method as in Example 4 were planted by the same method as in Example 4, for spraying the spray solution prepared above in (1) (at each spray volume of 300 L/10a) twice (28 days and 42 days after the planting of the seedlings) on the stems and leaves.

49 days after the start of the tests, all the plants in each lot were examined about the severity level of the disease to assess the frequency of the disease and the disease control value. Herein, the frequency of the disease and the disease control value were determined in the same manner as described above. The results of these tests are shown in Table 7. Because soft rot is a disease with damages hardly controlled, herein, even a chemical at the level C determined by the tests of the effects can practically be used.

TABLE 7

| Active ingredient (trade names) | Amount of active ingredient Spray volume | Determination of effect |
|---|---|---|
| Kresoxim-methyl (STROBY FL) | 500 g ai/10 a 150 L/10 a | C |
| Thiophanate methyl (Topsin M WP) | 1000 g ai/10 a 150 L/10 a | B |
| Boscalid (Cantus DF) | 500 g ai/10 a 150 L/10 a | C |
| Procymidon (Sumilex WP) | 500 g ai/10 a 150 L/10 a | A |
| Iprodion (ROVRAL 500 Aqua) | 500 g ai/10 a 150 L/10 a | B |
| Fludioxonil (Seibia FL) | 500 g ai/10 a 150 L/10 a | C |
| Mepanipyrim (Flupika FL) | 500 g ai/10 a 150 L/10 a | B |
| Oxytetracycline + streptomycin sulfate salt (Agrimycin WP) | 1/1500 300 L/10 a | D |

The onset of the disease in the non-treated lot in Table 7 was tested under conditions of high frequency where the mean level of the frequency of the disease was 49.5. The control effect of Agrimycin WP sprayed on the stems and leaves was at the level D (poorly effective), but the control effect of kresoxim-methyl was at the level C (effective at low level) and the control effect of thiophanate methyl was at the level B (effective). Further, the control effect of boscalid was at the level C (effective at low level) while the control effect of procymidone was at the level A (highly effective) and the control effect of iprodione was at the level B (effective). The control effect of fludioxonil was at the level C (effective at low level) and the control effect of mepanipyrim was at the level B (effective). It was confirmed that the control effects of such chemicals were higher than that of streptomycin as a control agent for soft rot, suggesting that the compounds exerted higher control effects against soft rot of Chinese cabbage.

Reference Test Example 4

Inhibition Test of Growth of Bacteria Causing Soft Rot of Potato

An inhibition test of the growth of bacteria causing the soft rot was done, when a control agent was directly applied to the bacteria causing the soft rot. A given volume of each pesticide of kresoxim-methyl (STROBY DF [trade name] manufactured by BASF), thiophanate methyl (Topsin M WP [trade name], manufactured by Nippon Soda Co., Ltd), boscalid (Cantus DF [trade name] manufactured by BASF), procymidone (Sumilex WP [trade name] manufactured by Sumitomo Chemical Agro Co., Ltd.) and streptomycin (Mycin Wettable powder [trade name] manufactured by Hokko Chemical Industry Co., Ltd.) was added together with a suspension of the bacteria causing the soft rot (*Erwinia carotovora*) to a preliminarily dissolved PSA culture medium (55 degrees Celsius) for subsequent thorough agitation, which was then spread on a plate for culturing at 27 degrees Celsius for 2 days, to examine the growth state. Subsequently, the formed colonies were examined according to the following three grades.

+: at the same level as the level of non-treated lot.

Plus or minus: apparently less than the colonies of the non-treated lot.

−: almost no colonies observed.

The results of these tests are shown in Table 8.

TABLE 8

| | Concentration of active ingredient (ppm) | | |
|---|---|---|---|
| Active ingredient | 1000 | 500 | 100 |
| Kresoxim-methyl (STROBY DF) | +, + | +, + | +, + |
| Thiophanate methyl (Topsin M WP) | +, + | +, + | +, + |
| Boscalid (Cantus DF) | +, + | +, + | +, + |
| Procymidone (Sumilex WP) | +, + | +, + | +, + |
| Streptomycin | 10 ppm −, − | 1 ppm −, − | |

Table 8 shows that kresoxim-methyl, thiophanate methyl, boscalid, and procymidone treated at an active ingredient concentration of 1,000 ppm against *Erwinia carotovora* never inhibited the growth, suggesting that the compounds had no direct antibacterial activity against *Erwinia carotovora*. In contrast, the antibiotic streptomycin at an active ingredient concentration of 1 ppm exerted a direct antibacterial activity against *Erwinia carotovora*.

Reference Test Example 5

Inhibition Test of Growth of Bacteria Causing Soft Rot of Potato

An inhibition test of the growth of bacteria causing the soft rot was done, when a control agent was directly applied to the bacteria causing the soft rot. A given volume of each pesticide of mepanipyrim (Flupika FL [trade name] manufactured by Nippon Soda Co., Ltd.) and streptomycin (Mycin Wettable powder [trade name] manufactured by Hokko Chemical Industry Co., Ltd.) was added together with a suspension of the bacteria causing the soft rot (*Erwinia carotovora*) to a preliminarily dissolved PSA culture medium (55 degrees Celsius) for subsequent thorough agitation, which was then spread on a plate for culturing at 27 degrees Celsius for 2 days, to examine the growth state. Subsequently, the formed colonies were examined according to the following three grades.

+: at the same level as the level of non-treated lot.
Plus or minus: apparently less than the colonies of the non-treated lot.
−: almost no colonies observed.
The results of these tests are shown in Table 9.

TABLE 9

| Active ingredient | Concentration of active ingredient (ppm) | | |
|---|---|---|---|
| | 1000 | 500 | 100 |
| Mepanipyrim (Flupika FL) | +, + | +, + | +, + |
| Streptomycin | 10 ppm −, − | 1 ppm +, ± | |

Table 9 shows that mepanipyrim treated at an active ingredient concentration of 1,000 ppm against *Erwinia carotovora* never inhibited the growth, suggesting that the compound had no direct antibacterial activity against *Erwinia carotovora*. In contrast, the antibiotic streptomycin at an active ingredient concentration of 10 ppm exerted a direct antibacterial activity against *Erwinia carotovora*.

Reference Test Example 6

Inhibition Test of Growth of Bacteria Causing Soft Rot of Potato

An inhibition test of the growth of bacteria causing the soft rot was done, when a control agent was directly applied to the bacteria causing the soft rot. A given volume of each pesticide of fludioxonil (Seibia FL [trade name] manufactured by Syngenta Japan K.K.), iminoctadine albesilate salt (Bellkute WP [trade name], manufactured by Nippon Soda Co., Ltd.), iprodione (Rovral WP [trade name] manufactured by Bayer Crop Science Co., Ltd.), and streptomycin (Mycin Wettable powder [trade name] manufactured by Hokko Chemical Industry Co., Ltd.) was added together with a suspension of the bacteria causing the soft rot (*Erwinia carotovora*) to a preliminarily dissolved PSA culture medium (55 degrees Celsius) for subsequent thorough agitation, which was then spread on a plate for culturing at 27 degrees Celsius for 3 days, to examine the growth state. Subsequently, the formed colonies were examined according to the following three grades.

+: at the same level as the level of non-treated lot.
Plus or minus: apparently less than the colonies of the non-treated lot.
−: almost no colonies observed.
The results of these tests are shown in Table 10.

TABLE 10

| Active ingredient | Concentration of active ingredient (ppm) | | |
|---|---|---|---|
| | 1000 | 500 | 100 |
| Fludioxonil (Seibia FL) | +, + | +, + | +, + |
| Iminoctadine albesilate salt (BELLKUTE WP) | +, + | +, + | +, + |
| Iprodione (Rovral WP) | +, + | +, + | +, + |
| Streptomycin | 10 ppm −, ± | 1 ppm +, + | |

Table 10 shows that fludioxonil, iminoctadine albesilate salt and iprodione treated at an active ingredient concentration of 1,000 ppm against *Erwinia carotovora* never inhibited the growth, suggesting that the compounds had no direct antibacterial activity against *Erwinia carotovora*. In contrast, the antibiotic streptomycin at an active ingredient concentration of 10 ppm exerted a direct antibacterial activity against *Erwinia carotovora*.

INDUSTRIAL APPLICABILITY

As a control agent with a control effect against soft rot and a control method for soft rot using the control agent, the invention has industrial applicability.

The invention claimed is:

1. An agent for treatment of a plant soft rot selected from a group consisting of:
   methyl, (E)-2-{2-[6-(2-cyanophenoxy)pyrimidin-4-yloxy]phenyl}-3-methoxyacrylate, methyl=(E)-methoxyimino[2-(o-tolyloxymethyl)phenyl]acetate;
   (E)-4-chloro-alpha,alpha,alpha-trifluoro-N-(1-imidazol-1-yl-2-propoxyethylidene)-o-toluidine, dimethyl=4,4'-(o-phenylene)bis(3-thioallophanate);
   (RS)—N-[2-(1,3-dimethylbutyl)-3-thienyl]-1-methyl-3-(trifluoromethyl)-1H-pyrazole-4-carboxamide, 2-chloro-N-(4'-chlorobiphenyl-2-yl)nicotinamide;
   2',4-dichloro-alpha,alpha,alpha-trifluoro-4'-nitro-m-toluenesulfone anilide;
   2,4,5,6-tetrachloro-1,3-benzene dicarbonitrile;
   N-(3,5-dichlorophenyl)-1,2-dimethylcyclopropane-1,2-dicarboximide, 3-(3,5-dichlorophenyl)-N-isopropyl-2,4-dioxoimidazolidine-1-carboxamide;
   N-(4-methyl-6-prop-1-ynylpyrimidin-2-yl)aniline; and
   1,1'-iminodi (octamethylene) diguanidinium=tris(alkylbenzenesulfonate),
   wherein the agent is a treatment agent to be applied to plant cultivation soil.

2. The agent for treatment of a plant soft rot according to claim 1, where the plant is vegetables.

3. The agent for treatment of a plant soft rot according to claim 2, where the vegetables are at least one selected from the group consisting of asparagus, endive, calla, cauliflower, cabbage, amorphophallus konjac, *Brassica campestris*, celery, Japanese radish, tobacco, onion, qing-geng-cai, tomato, eggplant, carrot, green onion, Chinese cabbage, *Brassica oleracea×Brassica campestris*, parsley, potato, broccoli, rakkyo, lettuce, wasabi, and oil-seed rape.

4. A treatment method for plant soft rot comprising:
   applying an effective amount of a compound having no antibacterial activity against *Erwinia carotovora* but having a control activity against fungi on soil surface to plant cultivation soil,
   wherein the compound is selected from a group consisting of:

methyl, (E)-2-{2-[6-(2-cyanophenoxy)pyrimidin-4-yloxy]phenyl}-3-methoxyacrylate, methyl, (E)-methoxyimino[2-(o-tolyloxymethyl)phenyl]acetate;

(E)-4-chloro-alpha,alpha,alpha-trifluoro-N-(1-imidazol-1-yl-2-propoxyethylidene)-o-toluidine, dimethyl=4,4'-(o-phenylene)bis(3-thioallophanate);

(RS)—N-[2-(1,3-dimethylbutyl)-3-thienyl]-1-methyl-3-(trifluoromethyl)-1H-pyrazole-4-carboxamide, 2-chloro-N-(4'-chlorobiphenyl-2-yl)nicotinamide;

2',4-dichloro-alpha,alpha,alpha-trifluoro-4'-nitro-m-toluenesulfone anilide;

2,4,5,6-tetrachloro-1,3-benzene dicarbonitrile;

N-(3,5-dichlorophenyl)-1,2-dimethylcyclopropane-1,2-dicarboximide, 3-(3,5-dichlorophenyl)-N-isopropyl-2,4-dioxoimidazolidine-1-carboxamide;

N-(4-methyl-6-prop-1-ynylpyrimidin-2-yl)aniline; and 1,1'-iminodi (octamethylene) diguanidinium=tris(alkylbenzenesulfonate).

5. The treatment method for plant soft rot according to claim 4, comprising applying an effective amount of a compound having no antibacterial activity against *Erwinia carotovora* but having a control activity against fungi on soil surface to the surface of the cultivation soil without mixing in the cultivation soil.

6. The treatment method for plant soft rot according to claim 4, where the amount of the compound with the control activity applied to the cultivation soil is 0.025 to 2.5 $g/m^2$.

7. The treatment method for plant soft rot according to claim 4, where the plant is vegetables.

8. The treatment method for plant soft rot according to claim 7, where the vegetables are at least one selected from the group consisting of asparagus, endive, calla, cauliflower, cabbage, amorphophallus konjac, *Brassica campestris*, celery, Japanese radish, tobacco, onion, qing-geng-cai, tomato, eggplant, carrot, green onion, Chinese cabbage, *Brassica oleracea*×*Brassica campestris*, parsley, potato, broccoli, rakkyo, lettuce, wasabi, and oil-seed rape.

9. A treatment method for plant soft rot comprising:

applying an effective amount of a compound having no antibacterial activity against *Erwinia carotovora* but having a control activity against fungi on soil surface to plant cultivation soil and subsequently sowing seeds of the plant or planting seedlings of the plant, wherein the compound is selected from a group consisting of:

methyl, (E)-2-{2-[6-(2-cyanophenoxy)pyrimidin-4-yloxy]phenyl}-3-methoxyacrylate, methyl, (E)-methoxyimino[2-(o-tolyloxymethyl)phenyl]acetate;

(E)-4-chloro-alpha,alpha,alpha-trifluoro-N-(1-imidazol-1-yl-2-propoxyethylidene)-o-toluidine, dimethyl=4,4'-(o-phenylene)bis(3-thioallophanate);

(RS)—N-[2-(1,3-dimethylbutyl)-3-thienyl]-1-methyl-3-(trifluoromethyl)-1H-pyrazole-4-carboxamide, 2-chloro-N-(4'-chlorobiphenyl-2-yl)nicotinamide;

2',4-dichloro-alpha,alpha,alpha-trifluoro-4'-nitro-m-toluenesulfone anilide;

2,4,5,6-tetrachloro-1,3-benzene dicarbonitrile;

N-(3,5-dichlorophenyl)-1,2-dimethylcyclopropane-1,2-dicarboximide, 3-(3,5-dichlorophenyl)-N-isopropyl-2,4-dioxoimidazolidine-1-carboxamide;

N-(4-methyl-6-prop-1-ynylpyrimidin-2-yl)aniline; and 1,1'-iminodi (octamethylene) diguanidinium=tris(alkylbenzenesulfonate).

10. The treatment method for plant soft rot according to claim 9, comprising applying an effective amount of a compound having no antibacterial activity against *Erwinia carotovora* but having a control activity against fungi on soil surface to the surface of the cultivation soil without mixing in the cultivation soil.

11. The treatment method for plant soft rot according to claim 9, where the amount of the compound with the control activity applied to the cultivation soil is 0.025 to 2.5 $g/m^2$.

* * * * *